(12) United States Patent
Taherian et al.

(10) Patent No.: US 6,781,371 B2
(45) Date of Patent: Aug. 24, 2004

(54) HIGH VERTICAL RESOLUTION ANTENNAS FOR NMR LOGGING

(75) Inventors: Reza Taherian, Sugar Land, TX (US); Boqin Sun, Concord, CA (US); Abdurrahman Sezginer, Los Gatos, CA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 10/064,994

(22) Filed: Sep. 6, 2002

(65) Prior Publication Data

US 2004/0046552 A1 Mar. 11, 2004

(51) Int. Cl.⁷ .............................................. G01V 3/00
(52) U.S. Cl. ....................................................... 324/303
(58) Field of Search ......................................... 324/303

(56) References Cited

U.S. PATENT DOCUMENTS

| | | | |
|---|---|---|---|
| 4,794,792 A | * 1/1989 | Flaum et al. ............ 73/152.05 |
| 5,646,533 A | * 7/1997 | Locatelli et al. ............ 324/339 |
| 5,796,252 A | 8/1998 | Kleinberg et al. |
| 5,834,936 A | * 11/1998 | Taicher et al. ............... 324/303 |
| 5,959,453 A | * 9/1999 | Taicher et al. ............... 324/303 |
| 6,018,243 A | * 1/2000 | Taicher et al. ............... 324/303 |
| 6,118,272 A | * 9/2000 | Taicher et al. ............... 324/303 |
| 6,121,774 A | 9/2000 | Sun et al. |
| 6,166,543 A | 12/2000 | Sezginer et al. |
| 6,229,308 B1 | 5/2001 | Freedman |
| 6,232,778 B1 | 5/2001 | Speier et al. |
| 6,255,818 B1 | 7/2001 | Heaton et al. |
| 6,326,785 B1 | 12/2001 | Kruspe |
| 6,400,147 B1 | 6/2002 | Toufaily et al. |
| 6,459,992 B1 | 10/2002 | Freedman et al. |
| 6,498,484 B1 | 12/2002 | Sun et al. |
| 6,518,757 B1 | 2/2003 | Speier |
| 6,522,137 B1 | 2/2003 | Sun et al. |
| 6,522,138 B2 | 2/2003 | Heaton |
| 6,525,535 B2 | 2/2003 | Reiderman et al. |
| 6,534,980 B2 | 3/2003 | Toufaily et al. |
| 6,541,969 B2 | * 4/2003 | Sigal et al. ................. 324/303 |
| 6,559,638 B1 | 5/2003 | Adelerhof |
| 6,573,716 B2 | 6/2003 | Toufaily et al. |
| 6,586,931 B2 | 7/2003 | Taicher |
| 2001/0033163 A1 | 10/2001 | Sigal et al. |

FOREIGN PATENT DOCUMENTS

| | | |
|---|---|---|
| GB | 2364129 | 1/2002 |
| WO | WO 99/24844 | 5/1999 |

OTHER PUBLICATIONS

RF Sigal et al, "A Method for Enhancing the Vertical Resolution of NMR Logs," *SPE 63215*, 2000 SPE Annual Technical Conference and Exh., Dallas, Tex. Oct. 1–4, 2000 (pp. 733–743).

\* cited by examiner

*Primary Examiner*—Diego Gutierrez
*Assistant Examiner*—Dixomara Vargas
(74) *Attorney, Agent, or Firm*—Kevin P. McEnaney; Brigitte L. Echols; John J. Ryberg

(57) ABSTRACT

A high vertical resolution antenna design is provided for use in an NMR measurement apparatus. Multiple coils are situated along the length of a magnet. A primary coil is energized to cause an oscillating magnetic field in a portion of earth formation surrounding a borehole. A secondary coil having smaller dimensions than the primary coil is operated to receive spin echoes from a depth of investigation associated with the secondary coil. A distance sufficient to minimize electrical coupling separates the coils. The separation distance can be reduced by selecting a secondary coil with orthogonal polarization to the primary coil. Alternatively, a cross coil configuration can be implemented where the orthogonal secondary coil at least partially overlaps the primary coil, thereby reducing the overall length necessary for the polarizing magnet.

62 Claims, 6 Drawing Sheets

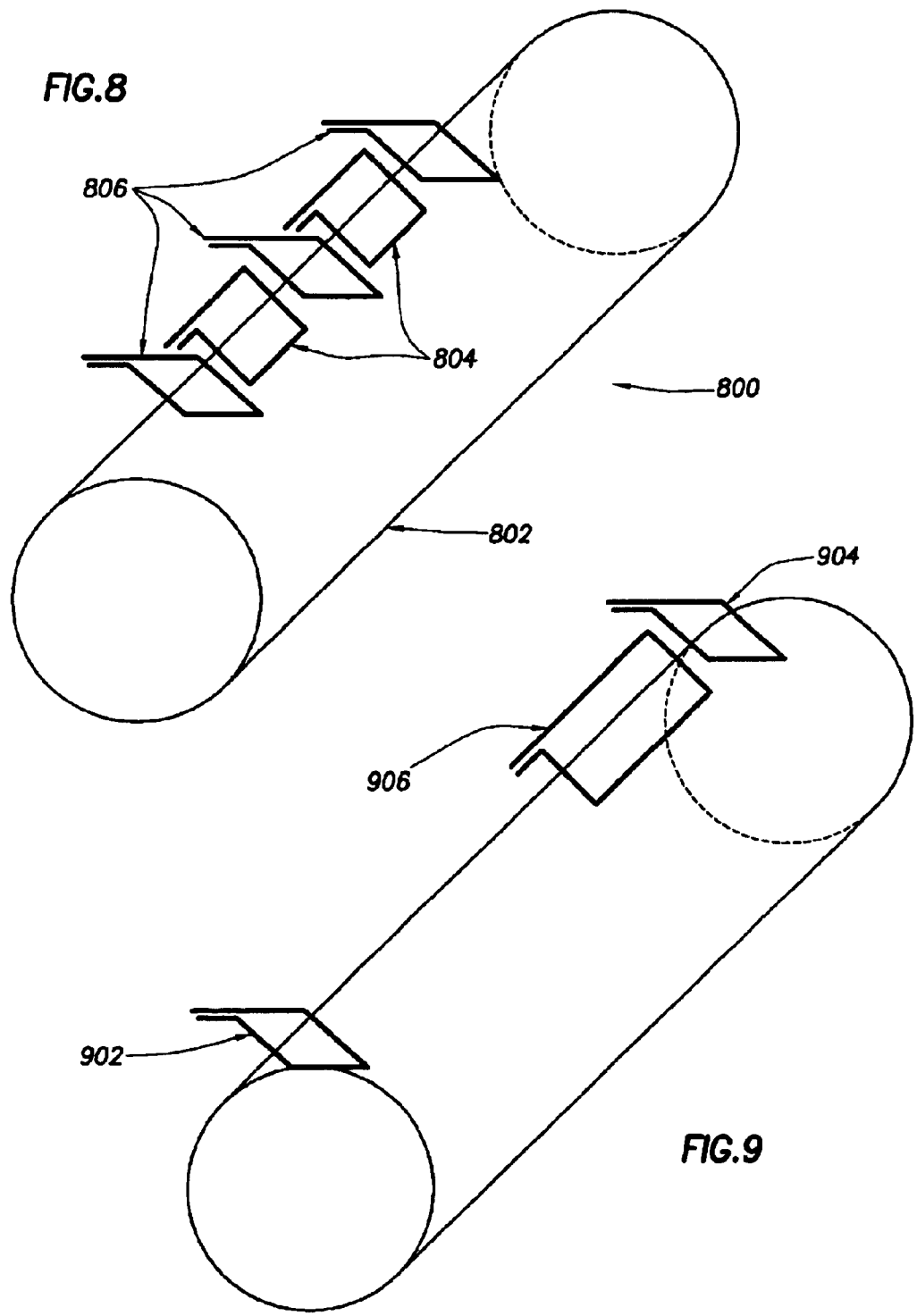

HIGH VERTICAL RESOLUTION ANTENNAS FOR NMR LOGGING

BACKGROUND OF INVENTION

1. Field of the Invention

This invention relates generally to nuclear magnetic resonance (NMR) apparatus and techniques for logging wells. More specifically, the invention relates to antenna designs for NMR well logging apparatus.

2. Background Art

Nuclear magnetic resonance (NMR) logging tools measure the amplitude and the decay constant of an NMR signal from the spin nuclei in earth formation, notably protons that are constituents of both water and hydrocarbons. The initial signal amplitude is a measure of total formation porosity while the time decay, invariably multi-exponential, can be decomposed into a distribution of exponential decays with different transverse relaxation times. The transverse relaxation time, $T_2$, is a measure of spin-spin interaction that provides information on the pore size, type of fluid, and hydraulic permeability of the formation. These parameters are important petrophysical quantities, explaining why NMR logging is popular.

The quality of NMR logs is strongly dependent on the signal to noise ratio, S/N, of the measurement. S/N is determined by the strength of the static magnetic field, the strength of the RF field, and the relative orientation of these two fields in the sensed region. The S/N also depends on the volume of the sensed region. In pulse NMR logging tools, a static magnetic field, $B_0$, along the z-axis, is used to polarize the nuclear spins, causing the individual spins to precess around $B_0$ at the so called Larmor frequency, $\omega$ L. In a typical measurement cycle, the RF field, $B_1$, is used to flip the magnetization to another plane, often perpendicular to the direction of static magnetic filed, to generate an NMR signal in the receiving antenna. The voltage induced at the output terminals of the receiving RF antenna due to a point magnetic dipole, such as a precessing nuclear spin, located at position r, is given by, $$V(r, \omega) = |\omega B_1(r, \omega).m/|(\omega) \quad (1)$$

Where, $\omega$ is the angular precession frequency, $B_1$ is the RF magnetic field generated by the antenna when it is excited by an RF current $I(\omega)$, and m is magnetic dipole moment of the nuclear spin. In macroscopic samples where many spins are present, a vector sum of m from all the spins in a unit volume constitutes the nuclear magnetization, $M_0$, which before the application of the RF pulse is aligned with $B_0$. Note that the signal is proportional to the scalar product of m (or for an ensemble of spins, $M_0$) and $B_1$, and thus is a maximum if $B_1$ and $M_0$ are aligned. This is why the RF antenna is designed so as in the sensing region the $B_1$ field is as perpendicular to $B_0$ as possible. This arrangement is to ensure that after the first 90 pulse, the magnetization and the B1 field are aligned. This is one of the conditions for maximizing the signal and increasing the S/N.

Another important parameter affecting the sensitivity of NMR measurement is the volume of sensed region. The total measured signal is the sum of the signal from all the excited spins in the sensed region and is given by:

$$S = \text{Integral}(V(r, \omega)dv) \quad (2)$$

Where, $V(r, \omega)$, given by Eq. 1 above, is the local NMR signal intensity from the spins in the differential volume element dv centered at r, and the integration is performed over the volume of sensed region.

For a gradient-type NMR logging tool operating at a frequency $\omega$, there are two ways of increasing the volume of sensed region. The first is to increase $B_1$ field strength, which causes the pulse length to decrease, this in turn increases the frequency content of the RF pulse, leading to a thicker sensed region in the radial direction. A second method is to increase the physical dimensions of the antenna, usually the antenna length. For the same antenna design, the length of the antenna is directly proportional to the length of the sensed region. In addition to its effect on the S/N, changing the length of antenna affects the optimum depth of investigation where the antenna is most efficient, the log speed effect, and the vertical resolution, discussed in more detail below.

In addition to increasing the volume of sensed region, a longer antenna is more suitable to transmit and receive for deeper depths of investigations. This is particularly attractive since at deeper depths of investigations the S/N of NMR is inherently lower.

Increasing the antenna length also reduces, but does not eliminate, the speed effect. When the antenna is used to apply a 90 pulse, the magnetization in front of the antenna is rotated into the transverse plane and is ready to be sampled. To sample the magnetization, using a CPMG sequence for example, one uses a series of 180 pulses, that are applied at a later time after the 90 pulse, during this time delay the tool/antenna has moved in the logging direction. At the time of the nth 180 pulse, the tool logging with a speed of v inches/sec, has traveled for $(2n-1)(\tau/2)v$ inches, where $\tau$ is the time between subsequent 180 pulses. This move causes the 180 pulse to be applied to the formation that is $(2n-1)(\tau/2)v$ inches shifted relative to the formation that was initially tipped by the 90 pulse. The result is an $(2n-1)(\tau/2)v$ inch of formation that has not been rotated into the transverse plane, and thus is not sampled properly. At the same time $(2n-1)(\tau/2)v$ inches of formation in which the spins have been rotated into the transverse plane, fall outside the viewing range of the antenna; these spins are "left behind". The spins in the "left behind" region do not sense the 180 pulse and do not contribute to the echo intensity. This leads to a loss of signal that is proportional to logging speed. This signal loss is termed herein as the speed effect—it is not present if the tool is stationary. For the same logging speed, as the length of the antenna (L) increases, the relative contribution of the signal from the spins that are left behind, $(2n-1)(\tau/2)v/L$, decreases and the speed effect is reduced.

A longer antenna samples a longer section of the formation, thus has a lower vertical resolution. This is a drawback for the measurement and limits the antenna length in NMR logging tools.

A typical antenna in NMR logging tools is oriented along the tool axis (axial direction). Due to the space restrictions in logging, if the antenna is designed for high efficiency (as opposed to high resolution), the axial-dimension of NMR antennas is longer than the tangential- and radial-dimensions. Electrically, these antennas have a radiation pattern that is approximately the same as that of a rectangular loop antenna oriented in the axial-tangential or axial-radial planes, see FIG. 1 for a pad tool example. Similarly, centralized logging tools utilize windings in the axial-tangential plane, shown in FIG. 2. These antennas are designed to have $B_1$ components orthogonal to $B_0$ in the sensed region, as is required by Eq. 1. The length of typical antennas, for example, is 24", defining the minimum vertical resolution of the tools. These antennas are designed with high S/N, having relatively low vertical resolution, and are termed herein as main or primary coils.

SUMMARY OF INVENTION

An antenna design is provided utilizing multiple antenna coils to obtain high vertical resolution NMR measurements of earth formations surrounding a borehole. This antenna can be used alone or in conjunction with the primary coil. A primary coil is situated across a longitudinal axis of a magnet. A secondary coil having smaller dimensions (and higher resolution) than the dimensions of the primary coil is also situated along the longitudinal axis of the magnet. The primary and secondary coils can be operated either independently or in combination to obtain NMR signals from a portion of an earth formation.

In a non-overlapping configuration, the secondary coil is spaced apart from the primary coil a distance that minimizes electrical coupling between the coils. If this is the case, the two antennas have to be operated in an active mode, each acting as both a transmitter and a receiver. In another non-overlapping antenna design, the secondary coil is situated in a cross coil configuration having its radiation polarization orthogonal to that of the primary coil, thereby minimizing the separation between the coils while maintaining electrical isolation.

A similar antenna configuration situates either a parallel high resolution coil or an orthogonal cross coil at a location along the magnet that overlaps the primary coil. The secondary coil is situated either partially overlapping or completely embedded within the primary coil. In either embodiment the secondary coil is operated in a receiver mode or a dual transmitter/receiver mode.

BRIEF DESCRIPTION OF DRAWINGS

FIG. 8 illustrates an antenna array according to the disclosed subject matter.

FIG. 9 illustrates another embodiment of an antenna array.

DETAILED DESCRIPTION

Figure 1A:
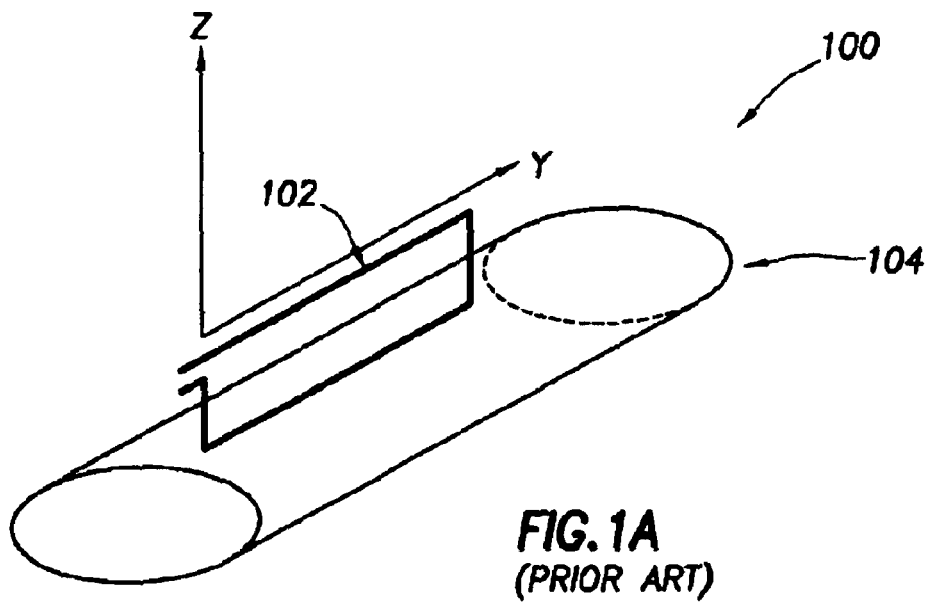
FIG. 1 illustrates prior art antenna designs for a pad type logging tool.
Figure 1B:
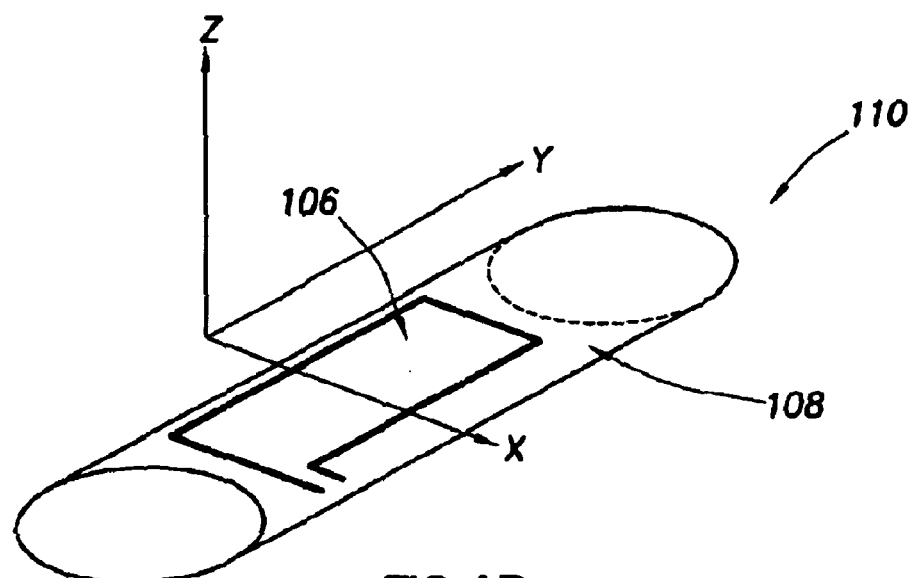
Figure 2:
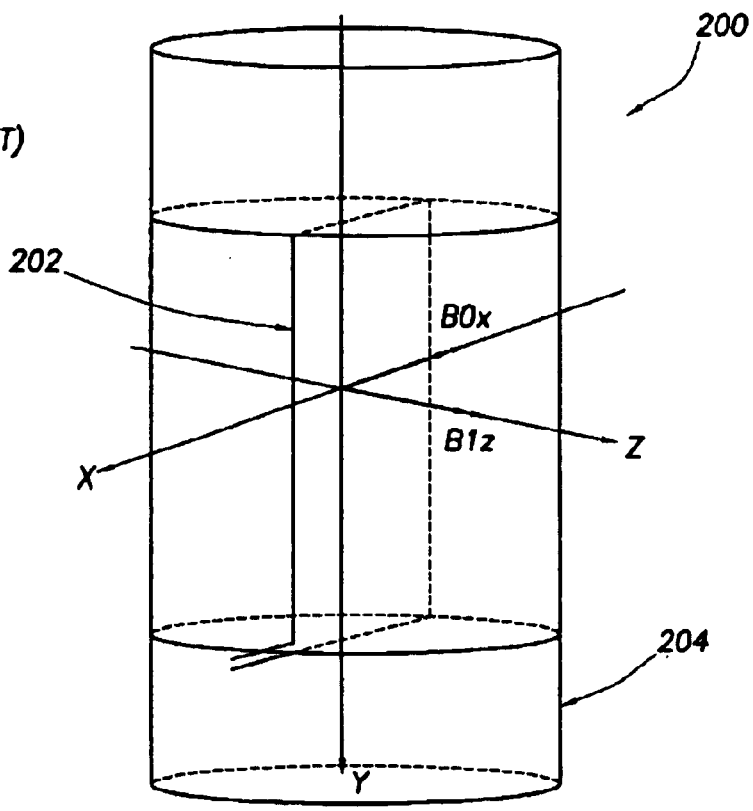
FIG. 2 illustrates a prior art antenna design for a centralized type logging tool.

As disclosed herein, additional, shorter antennas or secondary coils in NMR logging tools are utilized to compensate for the lower vertical resolution of a longer main antenna. Efficient design of these shorter, high resolution antennas is achieved in part by situating the high resolution antennas at various locations along the longitudinal axis of the magnet. For a high resolution antenna having a radiation direction that is parallel (HR antenna) to the primary antenna, a minimum spacing is utilized (but see the embedded embodiment discussed below) to minimize cross talk with the primary antenna (shown in FIGS. 1 and 2). For orthogonal high resolution cross coils (CHR antenna), the minimum distance from the primary coil can be reduced, thereby reducing the overall length of the magnet (shown in FIGS. 4 and 5). Both types of high resolution coils are operated as both a transmitter and a receiver, termed active mode.

Alternatively, the high resolution coils may be situated either partially overlapping or embedded within the primary coil. Both parallel and orthogonal coil designs can be implemented. Further, for each secondary coil design, the secondary coil can be operated in either an active mode, transmitter/receiver, or a passive mode, receiver only, or in dual mode.

In the following, we limit our discussion to the CPMG pulse sequence, but the proposed method is more general and is not limited to this particular pulse sequence. For example, pulse sequences such as the Carr-Purcell sequence, diffusion editing sequences (more fully disclosed in U.S. Pat. No. 5,796,252, to Kleinberg et al.) and inversion recovery sequences and others may be implemented without departing from the disclosed subject matter.

Independent High Resolution AntennaAccording to one embodiment, a HR antenna is implemented using a shorter version of the main antenna positioned on the magnet. An appropriate distance between the HR and main antennas will ensure negligible interaction (cross talk) between the two antennas. Since there is no cross talk, the HR antenna will operate completely independent of the main antenna. In this mode, termed herein as the active mode, the HR antenna acts as a transmitter as well as a receiver antenna.

Using a shorter HR antenna does not necessarily imply poor S/N. Although shortening the length of an antenna, while keeping all the other operational parameters the same, leads to a loss in signal, the depth of investigation of the HR antenna can be lowered to compensate for this loss. Thus, one embodiment consists of the HR antenna having a shallower depth of investigation compared to the primary antenna. Another embodiment comprises the primary and the HR antennas tuned to the same or similar depth of investigation.

Figure 3:
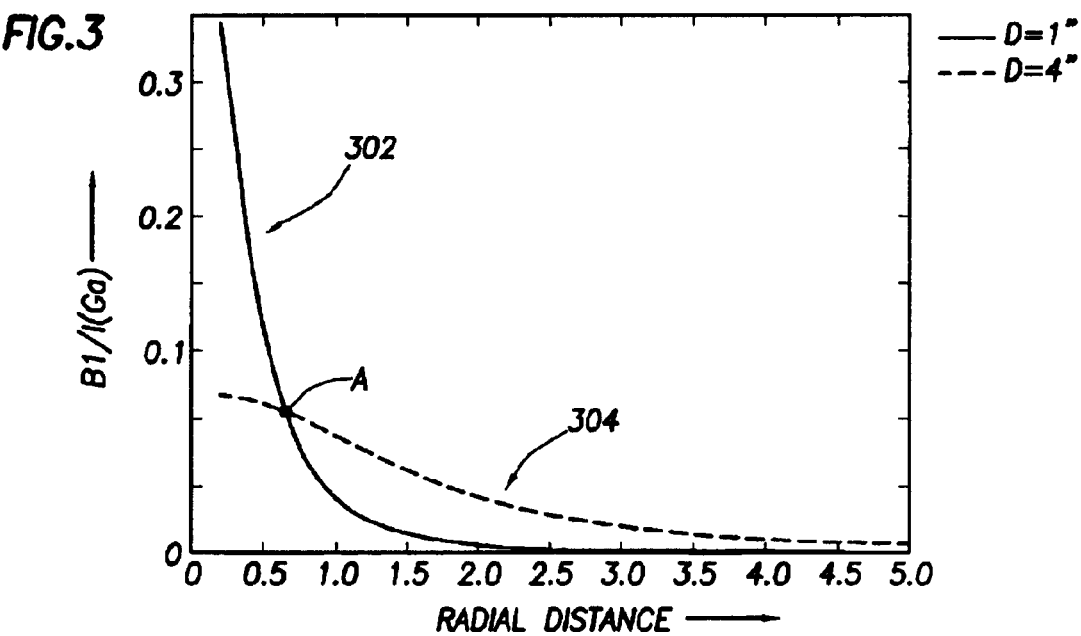
FIG. 3 is a graph depicting depth of investigation characteristics for an antenna design according to the disclosed subject matter.

There is a correlation between the physical length of the antenna and the optimum depth of investigation, DOI. Longer antennas are more appropriate for deeper depths of investigations. FIG. 3 demonstrates this point for simple loop antennas. In this figure, the magnetic field intensity, $B_1$, of a 1" and a 4" loop antenna, are plotted as a function of the radial depth of investigation. For the unit exciting current, the smaller loop, having smaller area, leads to higher flux density, and to a larger initial magnetic field intensity as measured along the axis of the antenna or loop. However, the magnetic field decays faster and crosses that of the larger loop. Past the crossing point A the smaller antenna is less efficient. Although the magnetic field from the larger antenna also diminishes deeper into the formation, the rate of loss is slower than that for the smaller antenna. Comparatively, the larger antenna is more efficient past the crossing point A than the smaller antenna. From FIG. 3, a 1" diameter loop is preferable to a 4" diameter loop antenna for DOIs of about less than 0.7 inch. Although this example is a simplified two-dimensional case, the general conclusion is valid for the three dimensional antennas used in logging tools.

In an NMR logging tool, the main antenna is usually designed to operate for a few different depths of investigations and its length is not optimum for shallower DOIs. The HR antenna on the other hand can be dedicated to a depth of investigation and designed to have highest sensitivity for that particular DOI, thus gaining back some of the signal loss resulting from its shorter physical length. Because, shallower depths of investigations have inherently higher NMR signal-to-noise ratios, dedicating the HR antenna for operation in a shallower DOI is one of the parameters in the designers disposal to ensure the results from this antenna have acceptable S/N.

The difference between S/N from the main antenna compared with the HR antenna depends on the relative lengths of the two antennas in addition to their actual depths of investigations. The shorter, HR antenna is more likely to suffer from logging speed or travel effect. As discussed above, the travel effect is directly proportional to the logging speed and inversely proportional to the length of the antenna. In extreme cases, the shorter HR antenna may run out of spins to sample. In this case, the tool may not be able to make NMR measurements for the length of time needed for a complete characterization of $T_2$ distribution. However, in most cases, it is possible to measure only the initial (perhaps 100) echoes, depending on the logging speed, echo spacing and the antenna length. Although this smaller dataset may not be sufficient to return the entire suite of NMR measurements, the initial intensity of this signal is enough to determine the total porosity, and the time dependence of the measured echo intensity will help measure the $T_2$ distribution from faster decaying spins such as bound fluids.

Alternatively, where the size of the antenna is too small or the logging speed is too fast to obtain a large enough sample, the apparatus may require that the logging speed be slowed. According an embodiment, a switch is implemented to automatically slow the logging speed. The switch is activated to slow logging speed when a processor within the tool senses that insufficient data is being received. Alternatively, activation of the HR antenna directly activates the switch to slow logging. Further, an alarm may be used to signal to a surface station a need to manually slow the logging operation.

Figure 4A:
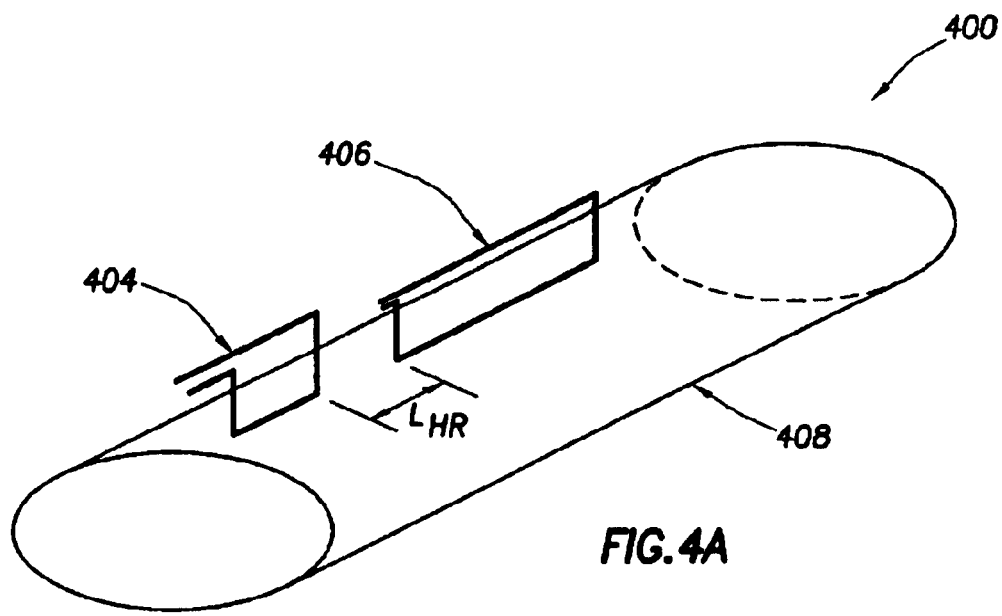
FIG. 4 illustrates antenna designs for a pad type logging tool according to the disclosed subject matter.
Figure 4B:
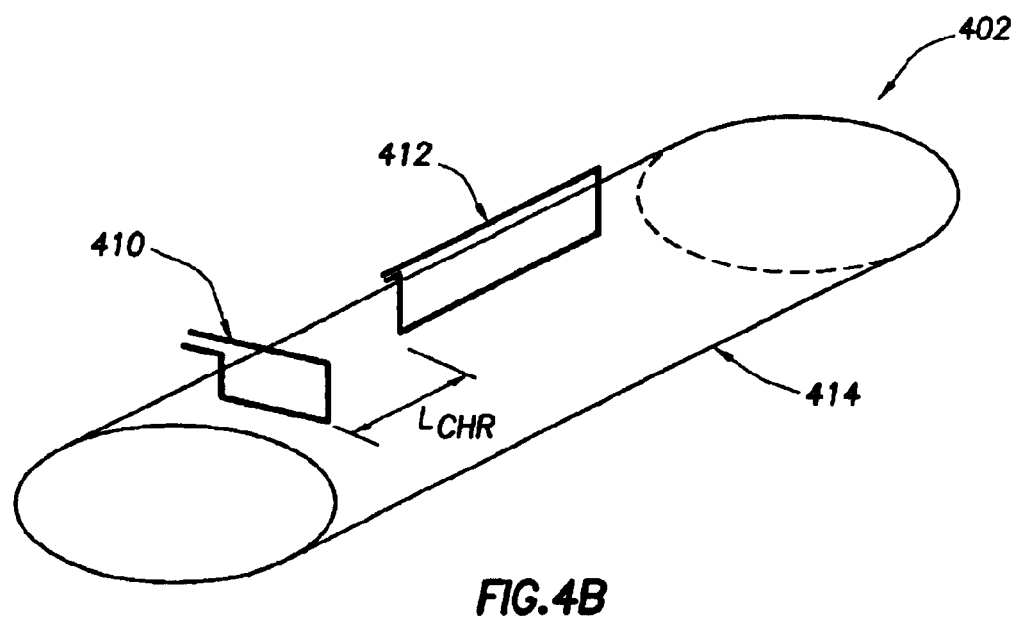

An exemplary configuration is shown in FIG. 4 where a primary and a secondary coil are situated in a non-overlapping manner. If the HR antenna has the same radiation direction as the main antenna, there can be a strong interaction (cross talk) between the two antennas. If the two antennas interact, the measurement from one antenna will contain information from the second. This may or may not be desirable depending on the particular application. Turning to FIG. 4, shown is a magnet/antenna configuration 400 according to one embodiment of the disclosed subject matter. HR antenna 404 and the main antenna 406 are separated from each other at a distance $L_{HR}$ to minimize the interaction. The configuration 400 is affected by the length of the magnet 408. When a long magnet is used sufficient separation for $L_{HR}$ may be possible, but with a short magnet, $L_{HR}$ can be too long for the magnet 408.

According to another embodiment, particularly suited to short magnet designs, the cross talk between the main and the HR antenna can be greatly reduced by using a secondary coil with a radiation polarization orthogonal or substantially orthogonal to that of the main antenna. Experimental results show for such cases a separation $L_{CHR}$ as small as 1.5 inches between the main antenna 412 and the cross HR antenna (CHR antenna) 410 is enough to reduce the cross talk by 30 dB. Since the separation distance can be shorter for a CHR antenna compared to an HR antenna, the disclosed multiple antenna design may be applied to NMR tools utilizing small magnets. In either configuration, the HR antenna 404 or the CHR antenna 410 is used to transmit the 90 pulse to tip the magnetization into the transverse plane and then to transmit the 180 pulses to generate spin echoes. In addition, the HR antenna 404 or CHR antenna 410 operate to receive the echoes. Since both excitation and receiving is performed by the same antenna, the HR antenna 404 or the CHR antenna 410 is considered to be an independent active antenna.

According to a similar embodiment, the HR 404 or the CHR antenna 410 in an active mode is operated in conjunction with the primary antenna 406 or 412 to obtain multiple NMR measurements from different regions of the formation. Specifically, both the primary and the secondary coils are operated as independent transmitter/receiver antennas. Each antenna is tuned to excite and receive spin echoes from different regions of the formation. For example, the primary coil receives spin echoes from a deep region while the secondary coil receives spin echoes from a shallow region. Further, the primary coil receives spin echoes over a longer region (in the axial direction of the borehole) than the secondary coil (hence a higher vertical resolution). Comparing these two sets of spin echoes improves the ability to detect certain formation attributes. For example, formation boundaries may be detected by correlating the vertical region tested by the primary antenna with the shorter vertical region tested by the secondary antenna. In addition, varying depth measurements such as a determination of fines invasion may be made by correlating the different depth regions investigated by the primary and the secondary coil. Other applications can be realized through various processing of the two data sets according to known techniques.

Figure 5:
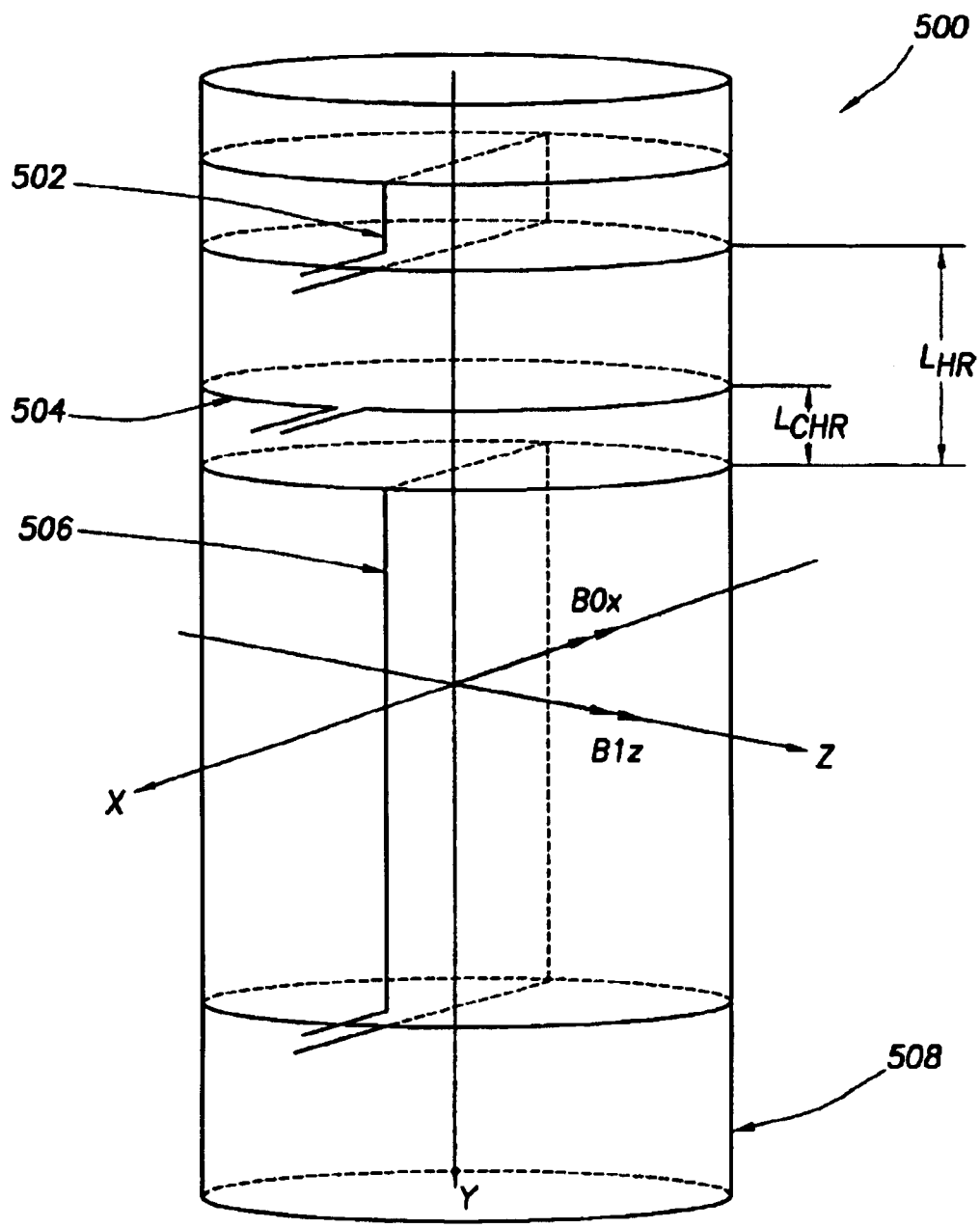
FIG. 5 illustrates an antenna designs for a centralized type logging tool according to the disclosed subject matter.

The HR antennas and CHR antennas can be used for both pad type and centralized NMR logging tools. In FIG. 4, shown are HR and CHR antennas in a pad tool. Turning to FIG. 5, shown are the HR and CHR antennas appropriate for centralized NMR logging tools. Specifically, HR antenna 502 is located at a distance $L_{HR}$ for the main antenna 506. As in the configurations of FIG. 4, because HR antenna 502 lies in the same plane as the main antenna 506, thus creating parallel magnetic fields, $L_{HR}$ must be a distance sufficient to minimize the amount of interaction or overlapping of the magnetic fields generated by the two antennas. The CHR antenna 504, on the other hand, can be located a distance $L_{CHR}$ which is much less than $L_{HR}$ from the main antenna 506, thereby minimizing the overall length of the magnet 508. It should be noted that the magnet/antenna configuration 500 is shown with both the HR antenna 502 and the CHR antenna 504 for illustration purposes only and is not intended to limit the scope of the disclosed subject matter. Instead, a centralized magnet/antenna configuration can include any combination of the main antenna 506 with both or either the HR antenna 502 and the CHR antenna 504. The embodiments discussed above with respect to pad tools are equally applicable for the centralized type tool designs such as shown in FIG. 5.

Figure 6:
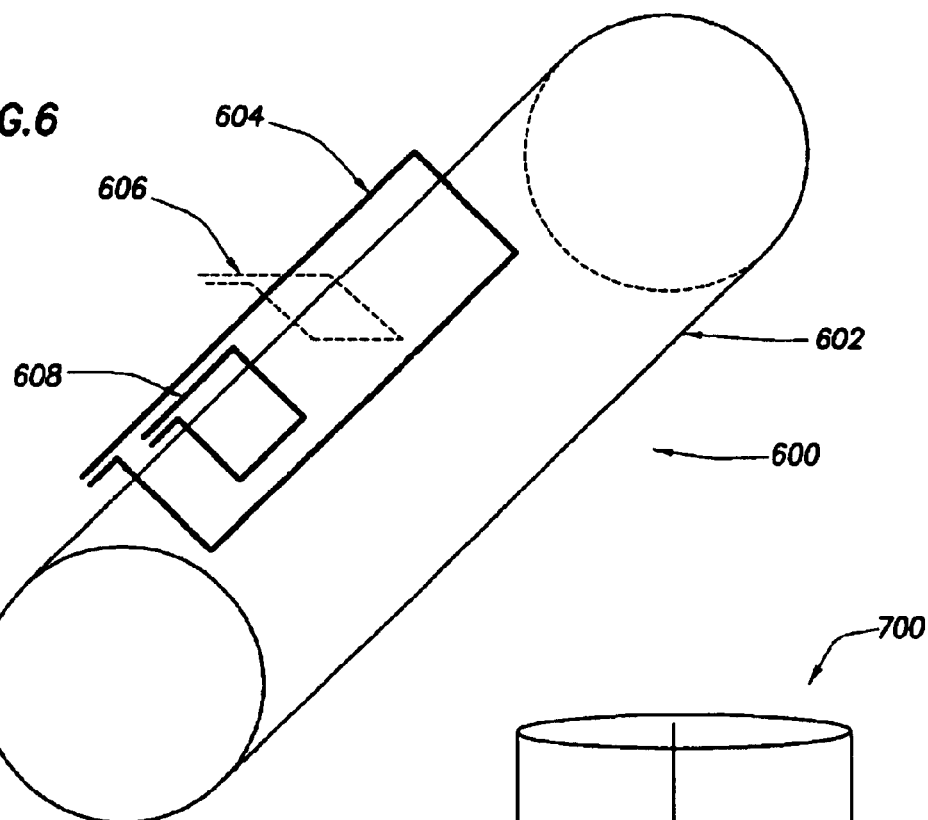
FIG. 6 illustrates embedded antenna designs for a pad type logging tool according to the disclosed subject matter.

Embedded High Resolution AntennaTurning to FIG. 6, another embodiment is to embed an HR antenna 608 or a CHR antenna 606 (dotted line) inside the main antenna 604. With respect to a parallel antenna configuration, because the embedded HR antenna 608 has the same radiation orientation as the main antenna 604, there is a potential for strong coupling between the two antennas. Without compensation, the main antenna 604 receives the signal from the total length of the sensed region and couples the signal to the short antenna 608. In this case, the vertical resolution of the HR antenna 608 is the same as the main antenna 604 and thus is not improved. For embedded HR antennas to be effective, the coupling to main antenna 604 must be minimized. Unlike the independent HR antenna 404, discussed above, in an embedded configuration separation of the two antennas is not a design option. However, cross-talk for embedded secondary antennas can also be avoided by placing the HR secondary coil 608(parallel to the primary coil) within the primary coil 604 in such a manner to reduce the mutual inductance between the two loops. Specifically, decoupling two antennas having similar radiation directions is achieved according to known methods. For example, Anderson, et al., WO 99/24844 illustrates positioning of coils which minimizes mutual inductance and is incorporated herein by reference. Furthermore, Mansfield WO 96/34296 shows how capacitors can be used to tune out or cancel the mutual inductance, also incorporated by reference.

Cross talk between an embedded antenna and a primary antenna can also be minimized using a CHR antenna 606. This is similar to the CHR antenna 410 discussed above, with the main difference being that the CHR antenna 606 is embedded inside the main antenna 604. As discussed in the non-overlapping embodiment, cross talk is reduced because the radiation patterns of the primary coil 604 and the CHR coil 606 are orthogonal or substantially orthogonal. Residual coupling can be tuned out according to Mansfield, WO 96/34296, or other known techniques.

According to one mode of operation of partially overlapping or embedded antenna, the main antenna 604 is used to generate 90 and 180 pulses, tipping the magnetization onto the transverse plane and producing spin echoes. The region of the formation that can be measured by this pulse sequence, called the sensed region of the main antenna 604, extends along the length, and is approximately as long as the length, of main antenna 604. If one detects the echoes from this entire region, which is what the main antenna does when used as receiver, the log vertical resolution is roughly the same as the length of the main antenna 604. In the case of one or more short antennas embedded inside the main antenna 604 for receiving the signal, the vertical resolution will be defined by the length of the shorter embedded antenna, rather than that of the main antenna 604. Thus even though a long section of formation is resonated, the signal from the HR antenna 606 or 608 is from a small portion of the sensed region, leading to higher vertical resolution.

One feature of the embedded antenna is an insensitivity of the embedded antenna to speed effects. Since the main antenna 604 is always longer than the secondary antenna 606 or 608, the resonated region is longer than the viewing region of the HR or CHR antenna. Unless the HR or CHR antenna is located on one of the two ends of the main antenna, the tool movement causes new, and resonated spins to come into the viewing region of the secondary antenna, compensating for the spins which are "left behind". For this reason, the embedded HR or CHR antenna has more immunity to the speed effect than the main antenna 604.

An important difference between this implementation of FIG. 6 and the independent HR antenna 400 of FIG. 4, is that for the embedded embodiment, the HR antenna 608 operates as a receiver only, which is termed the passive mode of operation. The main antenna 604 transmits all the high power RF pulses and the HR antenna 608 handles all low power received signals. The same is true for the CHR antenna 606 implementation.

According to a similar embodiment, the radiation direction of the main antenna 604 and the embedded secondary antenna need not be completely independent. In a CPMG pulse sequence, the first step is to apply a 90 pulse to rotate the magnetization into the transverse plane of rotating frame of reference. If the direction of the $B_1$pulse is in the x-direction, then at the end of the 90 pulse, $M_0$ is focused substantially along the y-direction. The spins, sensing different local magnetic fields, begin to defocus. After a time delay, t/2, a 180 pulse is applied along the y-axis to reverse the direction of precession. This causes the spins to refocus, and after another t/2 seconds, generation of a spin echo. In the laboratory frame of reference, the focused spins precess in the x-y plane at Larmor frequency, $\omega$ L. The echo is detected anytime M is aligned with the radiation direction of the receiving antenna (x-axis in our example), thus the amplitude of the measured echo is modulated by $\omega$ L.

Since M constantly precesses in the x-y plane, its detection is not limited by the antennas that are sensitive to x-direction or HR antenna. M can be detected at any orientation in the x-y plane (i.e., the detectable signal is circularly polarized). The echo signal can also be detected if there is a receiver antenna oriented along the y-axis, for example. A separate antenna with radiation direction oriented orthogonal, for example CHR antenna 606, to the main antenna 604 (y-direction) is able to detect the echoes in the y-direction, and has the advantage of reduced cross talk with the main antenna 604.

Receiving the echoes is not limited to the HR and CHR antennas. Both the main and the secondary antennas can sample the echoes at the same time. One advantage of such a dataset is that one can compare or combine the low resolution data (from the main antenna) with the high resolution data (from the CHR antenna) to generate different measurement results. For example, combined processing of the two datasets can be used to improve the resolution of the log from the main antenna, for example by combining the high resolution data with the low resolution data to compensate logging speed effects associated with the primary antenna. An estimate of spin-spin relaxation times can be calculated based on the combined data from the high resolution antenna and the primary antenna. Also, when the main antenna is at a bed boundary, signal measurements are received from both earth layers. However, the CHR antenna can lie within only one earth layer. The combined data can be used to separate the NMR response measured by the main antenna for each individual layer.

According to another embodiment, the secondary antenna is operated in an active mode while the main antenna is operated in a passive mode. Since a small section of the formation has been tipped by the 90 degree pulse, both antennas measure a high resolution log. In yet another embodiment, both antennas can be operated in an alternating mode. For example, if the CHR antenna is used to generate the 90 degree pulse, while the main antenna generates subsequent 180 degree pulses, both antennas provide a high resolution log. However, only the log from the CHR antenna is affected by logging speed. Comparing the two logs provides additional information that can be used to determine relaxation processes. In addition to those specifically described herein, many combinations of using the primary and secondary antennas together can be implemented with only minor modifications to the disclosed subject matter.

Where the secondary antenna is operated in the passive mode, one advantage obtained is an immunity to acoustic ringing. In pulse NMR instruments where the RF antenna is used as transmitter as well as a receiver, the high power RF pulse, during transmission, induces magnetoacoustic ringing in the antenna and its surroundings. This ringing is relatively long lived and often interferes with echo detection when the same antenna is used as receiver. A passive cross coil, however, is not exposed to high power pulses thus there is no ringing in the secondary antenna. In addition, for an embedded passive CHR antenna, because the CHR antenna radiation polarization is substantially orthogonal to the transmitting antenna, it is largely immune to the acoustic ringing induced by the main antenna.

Yet another advantage of CHR antennas as a passive receiver is apparent in the design of the tool electronics. The receiver electronics connected to an active antenna must handle relatively high voltages at the time of RF pulse transmission, while also having the sensitivity for measurement of very low voltages at the time of received signals. This is a stringent design requirement on the electronic circuitry and should be avoided whenever possible. The passive CHR antenna is exposed to only the low voltages and thus its detection circuitry is simplified.

Figure 7:
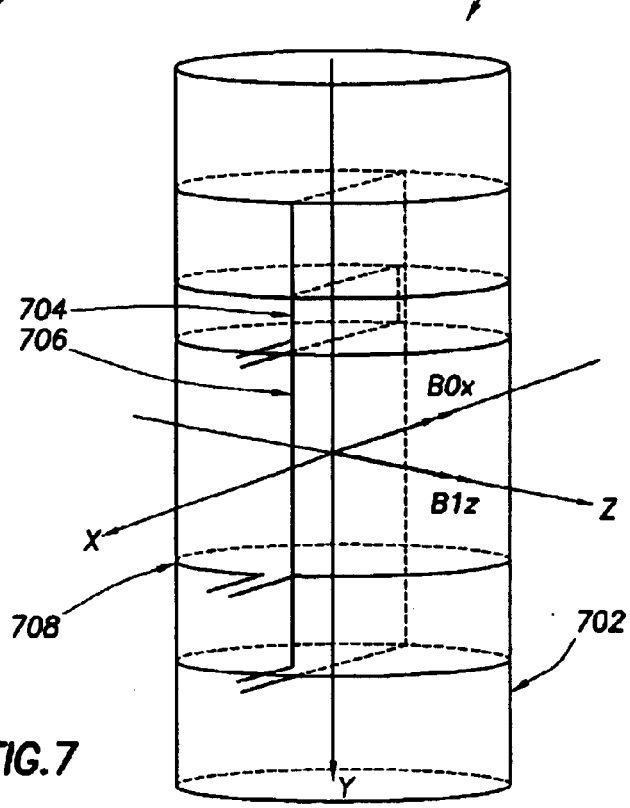
FIG. 7 illustrates embedded antenna designs for a centralized type logging tool according to the disclosed subject matter.

Turning to FIG. 7, shown is a design of a centralized tool 700 with embedded HR and CHR antennas. Specifically, embedded HR antenna 704 or CHR antenna 708 is located within the overall length of the main antenna 706. The CHR antenna 708 is wound orthogonal or substantially orthogonal to the windings of main antenna 706. As can be seen, the overall length requirement for magnet 702 is further reduced compared to the CHR antenna 504 of FIG. 5. Here again, the CHR antenna 708 or the HR antenna 704 may be operated in a passive mode, receiving spin echoes generated in response to the RF pulses emitted by the main antenna 706 or in an active mode as both a transmitter of at least a portion of the excitation sequence and as a receiver of the induced spin echoes.

Although the exemplary embodiments for embedded antennas have been discussed in fully embedded configurations, similar design considerations and advantages equally apply for configurations of both HR and CHR antennas which are only partially embedded or only partially overlap a region of the main antenna.

Array of HR Antennas Turning to FIG. 8, another embodiment utilizes an array of HR antennas. Where more than one HR antenna is present, the separation between adjacent antennas needs to be a large enough to reduce their cross talk to an acceptable limit. A strong coupling between two antennas is equivalent to detecting a signal from both antennas simultaneously and reduces the vertical resolution of the measurement thus defeating the purpose of using these antennas. To compensate for this, FIG. 8 illustrates an embodiment in which HR antennas 804 and CHR antennas 806 are alternated without a main antenna. Alternating the antennas avoids the requirement for like-oriented antennas to be spaced far enough apart to minimize the cross talk between them, which in turn would limit the number of antennas that can be placed either inside a main antenna in an embedded configuration or the number of antennas that can be placed across the length of the magnet 802. Also, if a main antenna were present and used as a receiver, the result would be a lower resolution measurement over the entire length of the sensitive region. An arrangement similar to that of FIG. 8 can be used to form HR antenna arrays for centralized tools in a manner similar to that discussed above for application of pad-type configurations to centralized tools.

The array of HR antennas can be used to increase the coverage of the measurements. For example, in GB 2364129, antenna arrays have been designed for other applications such as borehole imaging. In the context of obtaining high resolution depth measurements, rather than moving the same HR antenna from one depth along the borehole to the next, the array will generate a high resolution log for many borehole depths all at the same time. In this embodiment, the number of depth positions is equivalent to the number of antennas. Another advantage of an antenna array is that different antennas have different pre-polarization times, as disclosed in U.S. Pat. No. 6,255,818. The first antenna will have the shortest pre-polarization time and the last antenna will have the longest pre-polarization. By comparing measurements from the entire set of antennas, a $T_1$ distribution is derived using the high resolution results measured by the HR antennas. The antennas in the array are envisioned as individual active antennas, i.e. each antenna acts as transmitter as well as receiver.

Turning to FIG. 9, another embodiment utilizes at least one secondary coil on the extreme up-hole side of the magnet (UHHR) 902 and another secondary coil on the extreme down-hole side of the magnet (DHHR) 904. The main antenna 906 is placed between the two, preferably closer to the down-hole side of the magnet. This embodiment enables the main 906 and the DHHR 904 antennas to have long pre-polarization time for up logging (logging while the tool is moving up). The measurements from main antenna 906 is used for a normal NMR log while the measurement from DHRR antenna 904 is use for a high-resolution log. In up logging the UHHR antenna 902 has a small pre-polarization and its measurement, combined with that from DHHR antenna 904 (after depth matching), can be used to estimate T1 as discussed above. In down logging, where the measurements are done when the tool is traveling down the hole, the role of the UHHR antenna 902 and the DHHR antenna 904 are interchanged. The UHHR antenna 902 has the long pre-polarization while the DHHR antenna 904 has a short pre-polarization. In this case, the measurement from UHHR can be used for a high-resolution log, while the combination of the measurements from the two HR antennas can be used to estimate T1. The main antenna 906 may be placed closer to the UHHR antenna 902 to obtain measurements from main antenna in down logging, or alternatively two different main antennas used.

In another embodiment, more than one CHR antenna, without HR antennas, are embedded in the main antenna. In this embodiment, the high resolution component of the antenna design is the CHR array while the main antenna is a single long antenna. Here the CHR antennas cannot be too close to each other since they have the same radiation pattern that is orthogonal to the that of the main antenna. Nonetheless, having more than one embedded CHR antenna leads to new information and better high resolution coverage without sacrificing the performance of the main antenna. In such an arrangement, as with a single embedded CHR, any one of the antennas can act as an active or passive antenna. For example, one of the CHR antennas can be programmed as an active antenna transmitting 180 and 90 degree pulses in combination with the main antenna and receiving spin echoes while another CHR antenna in the same array can be programmed as a passive antenna merely receiving spin echoes induced by the main antenna or other CHR antennas or both.

Furthermore, the disclosed antenna configurations are effective for high resolution measurements in both wireline and while drilling NMR tools. Minor modifications such as placement of the secondary antennas can be made to account for the differences in the logging mode. For example, in a while drilling application, logging is typically performed at a lower rate than logging in a wireline application. In such a case, because the logging speed effects are diminished, placement of the secondary antenna may be available for while drilling applications that are not possible for wireline applications.

The forgoing disclosure and description of the various embodiments are illustrative and explanatory thereof, and various changes to the NMR acquisition sequence, the logging process, the materials utilized in the antenna design, the organization of the components and the order and timing of the steps taken, as well as in the details of the illustrated system may be made without departing from the disclosed subject matter.

What is claimed is:

1. An NMR measurement apparatus, comprising:
   a permanent magnet,
   a primary coil extending across a first surface area, the primary coil having a first depth of investigation and a first vertical resolution and producing a primary RF field in a volume of earth formation;
   a secondary coil extending across a second surface area, the second surface area less than the first surface area, the secondary coil having a second depth of investigation and a second vertical resolution and producing a secondary RF field in a volume of earth formation, the second vertical resolution higher than the first vertical resolution;
   a circuit coupled to the primary coil and the secondary coil adapted to perform high resolution NMR measurements of an earth formation based on a signal received by the second coil.

2. The NMR measurement apparatus of claim 1, wherein the NMR measurements comprise a secondary coil dataset associated with NMR measurements made for a depth of investigation associated with the secondary coil.

3. The NMR measurement apparatus of claim 2, wherein a high resolution log is, generated based on the secondary coil dataset.

4. The NMR measurement apparatus of claim 2, wherein the NMR measurements further comprising a primary coil dataset associated with NMR measurements made for a depth of investigation associated with the primary coil.

5. The NMR measurement apparatus of claim 4, wherein a spin-spin relaxation estimate based on a combination of the primary coil dataset and the secondary coil dataset.

6. The NMR measurement apparatus of claim 1, wherein the depth of investigation of the secondary coil is shallower than a depth of investigation of the primary coil.

7. The NMR measurement apparatus of claim 1, wherein the depth of investigation of the secondary coil is substantially the same depth as the depth of investigation of the primary coil.

8. The NMR measurement apparatus of claim 1, wherein the NMR measurement apparatus is a centralized-type logging tool.

9. The NMR measurement apparatus of claim 1, wherein the secondary RF field is orthogonal to the primary RF field.

10. The NMR measurement apparatus of claim 1, wherein a size of the secondary coil is optimized based on a combination of the depth of investigation of the secondary coil and the primary coil and the vertical resolution of the secondary coil and the primary coil.

11. The NMR measurement apparatus of claim 1, wherein the NMR measurements are made while drilling a borehole.

12. The NMR measurement apparatus of claim 1, wherein the primary coil and the secondary coil are arranged in a non-overlapping configuration along the axis of the apparatus.

13. The NMR measurement apparatus of claim 12, wherein the secondary antenna is located near a proximate end of the main antenna measured along the longitudinal axis of the NMR measurement apparatus.

14. The NMR measurement apparatus of claim 12, wherein the secondary coil is located a distance from the primary coil that minimizes an electrical coupling between the secondary coil and the primary coil.

15. The NMR measurement apparatus of claim 12, wherein the second coil is operated in an active mode as both a transmitter and a receiver.

16. The NMR measurement apparatus of claim 15, wherein the secondary antenna selectably transmits a portion of an NMR acquisition sequence.

17. The NMR measurement apparatus of claim 15, wherein the primary coil is selectably operated in either a passive or active mode.

18. The NMR measurement apparatus of claim 1, wherein at least a portion of the first surface area overlaps the second surface area.

19. The NMR measurement apparatus of claim 1, wherein the secondary antenna is embedded in the primary antenna.

20. The NMR measurement apparatus of claim 19, wherein the second coil is operated in a passive mode as a receiver of signals produced in response to a transmission by the first coil.

21. The NMR measurement apparatus of claim 19, wherein the second coil is operated in an active mode as both a transmitter and a receiver.

22. The NMR measurement apparatus of claim 21, wherein the secondary antenna selectably transmits a portion of an NMR acquisition sequence.

23. The NMR measurement apparatus of claim 21, wherein the primary coil is selectably operated in either a passive or active mode.

24. The NMR measurement apparatus of claim 1, the secondary coil further comprising:
   an array of secondary coils arranged in a non-overlapping configuration along the axis of the apparatus.

25. The NMR measurement apparatus of claim 24, wherein the array of the secondary coils comprises a pair of secondary coils, each of the pair of secondary coils situated at opposite proximate ends of the primary coil measured along the longitudinal axis of the NMR apparatus.

26. A method for obtaining high-resolution NMR measurements of an earth formation from an NMR apparatus having a magnet, a primary coil and at least one secondary coil, the method comprising steps of:
   producing a static magnetic field in the earth formation with the magnet;
   transmitting at least a portion of an RF pulse sequence with the primary coil extending across a first surface area to produce an oscillating magnetic field that is substantially orthogonal to the static magnetic field;
   receiving NMR signals with the secondary coil extending across a second surface area, the second surface area less than the first surface area, the secondary coil having a higher vertical resolution than a vertical resolution of the primary coil; and
   calculating at least one high resolution measurement based on the received NMR signals from the secondary coil.

27. The method of claim 26, further comprising:
   generating a secondary coil dataset associated with NMR measurements made for a depth of investigation associated with the secondary coil.

28. The method of claim 27, further comprising:
generating a high resolution log is based on the secondary coil dataset.

29. The method of claim 27, further comprising:
receiving NMR signals with the primary coil;
generating primary coil dataset associated with NMR signals from a depth of investigation associated with the primary coil.

30. The method of claim 29, further comprising:
calculating a spin-spin relaxation estimate based on a combination of the primary coil dataset and the secondary coil dataset.

31. The method of claim 26, wherein the depth of investigation of the secondary coil is shallower than a depth of investigation of the primary coil.

32. The method of claim 26, wherein the depth of investigation of the secondary coil is substantially the same depth as the depth of investigation of the primary coil.

33. The method of claim 26, wherein the NMR measurement apparatus is a centralized-type logging tool.

34. The method of claim 26, wherein the secondary RF field a orthogonal to the primary RF field.

35. The method of claim 26, further comprising the step of:
optimizing the size of the secondary based on a combination of the depth of investigation of the secondary coil and the primary coil and the vertical resolution of the secondary coil and the primary coil.

36. The method of claim 26, the calculating step further comprising calculating the high resolution measurement while drilling a borehole.

37. The method of claim 26, wherein the primary coil and the secondary coil are arranged in a non-overlapping configuration along the axis of the apparatus.

38. The method of claim 37, wherein the secondary antenna is located near a proximate end of the main antenna measured along the longitudinal axis of the NMR measurement apparatus.

39. The method of claim 37, wherein the secondary coil is located a distance from the primary coil that minimizes an electrical coupling between the secondary coil and the primary coil.

40. The method of claim 37, wherein the second coil is operated in an active mode as both a transmitter and a receiver.

41. The method of claim 40, wherein the secondary antenna selectably transmits a portion of an NMR acquisition sequence.

42. The method of claim 40, wherein the primary coil is selectably operated in either a passive or active mode.

43. The method of claim 26, wherein at least a portion of the first surface area overlaps the second surface area.

44. The method of claim 26, wherein the secondary antenna is embedded in the primary antenna.

45. The method of claim 44, wherein the second coil is operated in a passive mode as a receiver of signals produced in response to a transmission by the first coil.

46. The method of claim 44, wherein the second coil is operated in an active mode as both a transmitter and a receiver.

47. The method of claim 46, wherein the secondary antenna selectably transmits a portion of an NMR acquisition sequence.

48. The method of claim 46, wherein the primary coil is selectably operated in either a passive or active mode.

49. The method of claim 26, the secondary coil further comprising:
an array of secondary coils arranged in a non-overlapping configuration along the axis of the apparatus.

50. The method of claim 49, wherein the array of the secondary coils comprises a pair of secondary coils, each of the pair of secondary coils situated at opposite proximate ends of the primary coil measured along the longitudinal axis of the NMR apparatus.

51. The method of claim 49, the array of secondary coils further comprising:
a first plurality of secondary coils having a radiation polarization orthogonal to a radiation polarization of the primary coil; and
a second plurality of secondary coils having a radiation polarization parallel to the radiation polarization of the primary coil, wherein the secondary coils of the first plurality are alternated with the secondary coils of the second plurality.

52. An NMR measurement apparatus comprising: a permanent magnet; an array of coils situated along a longitudinal axis of the apparatus, wherein at least one coil of the array of coils has a higher vertical resolution than a vertical resolution of at least one other coil of the array of coils; and a circuit coupled to the array of coils adapted to perform high resolution NMR measurements of an earth formation.

53. The NMR measurement apparatus of claim 52, wherein at least two coils of the array of coils have different pre-polarizations times.

54. The NMR measurement apparatus of claim 52, wherein a spin-lattice relaxation estimate based on a combination spin echo measurements from at least two of the array of coils.

55. The NMR measurement apparatus of claim 52, wherein at least one coil of the array of coils is operated in an active mode as both a transmitter and a receiver.

56. The NMR measurement apparatus of claim 55, wherein at least one of the active coils transmits a portion of an NMR acquisition sequence.

57. The NMR measurement apparatus of claim 55, wherein at least one coil of the array is selectably operated in either a passive or active mode.

58. The NMR measurement apparatus of claim 52, the array of coils further comprising:
A first plurality of coils;
A second plurality of coils having a radiation polarization orthogonal to a radiation polarization of the first plurality of coils, wherein the coils of the first plurality are alternated with the coils of the second plurality.

59. The NMR measurement apparatus of claim 52, the array of coils comprising:
a primary coil extending across a first surface area, the primary coil having an associated depth of investigation and an associated vertical resolution and producing an RF field in a volume of earth formation;
a plurality of secondary coils, each secondary coil extending across a second surface area, the second surface area less than the first surface area, the secondary coil for receiving spin echoes from a volume of an earth formation at a depth of investigation associated with the secondary coil.

60. The NMR measurement apparatus of claim 59, wherein the plurality the secondary coils comprises a pair of secondary coils, each of the pair of secondary coils situated at opposite proximate ends of the magnet measured along the longitudinal axis of the NMR measurement apparatus.

61. The NMR measurement apparatus of claim 60, wherein the primary coil is situated between a pair of secondary coils.

62. The NMR measurement apparatus of claim 60, wherein the each coil of the pair of secondary coils has a different pre-polarization time.

* * * * *